United States Patent [19]

Takatori et al.

[11] Patent Number: Plant 5,316

[45] Date of Patent: Oct. 30, 1984

[54] ASPARAGUS PLANT—M138

[75] Inventors: Frank H. Takatori; Franklin D. Souther, both of Riverside, Calif.

[73] Assignee: The Regents of the University of California, Berkeley, Calif.

[21] Appl. No.: 467,729

[22] Filed: Feb. 18, 1983

[51] Int. Cl.[3] ..... A01H 5/03

[52] U.S. Cl. ..... Plt./89

[58] Field of Search ..... Plt./89

*Primary Examiner*—Robert E. Bagwill

*Attorney, Agent, or Firm*—Townsend and Townsend

[57] ABSTRACT

A new and distinct variety of male asparagus plant characterized by its vigorous and multi-stalked growth, its ability to initiate between 25 and 35 canes per season and which is also characterized by its high branching (above the 16th node) and earliness of spear emergence—a characteristic transmitted to its progenies.

3 Drawing Figures

DESCRIPTION

This invention relates to a new and distinct male clone of asparagus designated as M138. Plant M138 was selected from a line designated as S108 which was an open pollinated cross of female plant ($R_3P_{14}$) variety U.C.309 which was planted at the University of California Agricultural Experiment Station, Moreno, Calif., in 1964. The source of seed for the U.C.309 planting was obtained from Mr. J. Hanna, formerly a member of the Department of Vegetable Crops, University of California, Davis, Calif.

Male plant M138 is a vigorous growing multi-stalked plant. An established M138 plant, three years or older in age, will initiate between 25 and 35 canes per season. The diameter of the canes measured at soil level will range between three-fourths and one inch in diameter.

Plant growth is erect and the foliage, referred to as fern, will exceed six feet in height with lateral branches extending about three feet in all directions. The foliage is Light Hellebore Green (Plate XVII) and the stalks a Kildare Green (Plate XXXI) in color when mature. The first lateral branching occurs about 17.5 inches above soil level and exhibits a plant characteristic referred to as "high branching". The emergence of spears in the spring as soil temperatures increase, is early. The plant characteristic of "earliness" in spear emergence is transmitted to its progenies and is a particularly distinguishing one when compared to other known varieties of asparagus.

Asparagus is a dioecious plant, individual plants being either male or female in sex.

Figure 1:
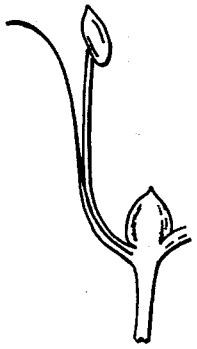
FIG. 1 shows the typical male parts of M138.
Figure 2:
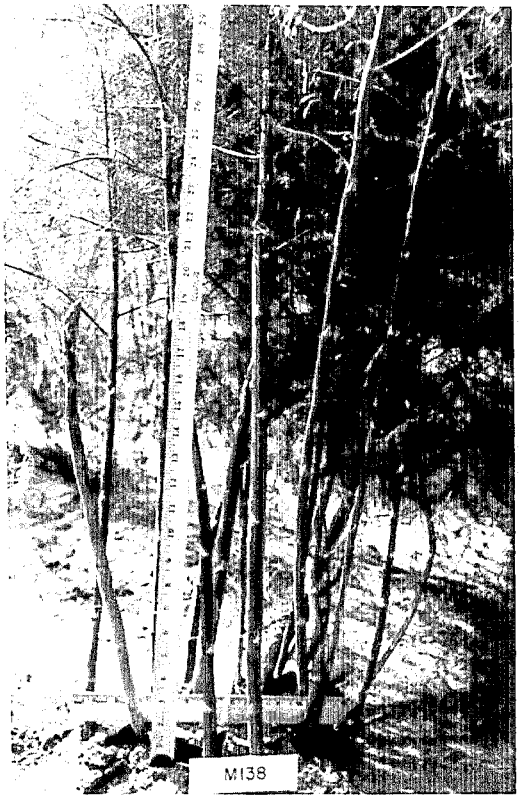
FIG. 2 shows the "high branching" characteristic of M138.
Figure 3:
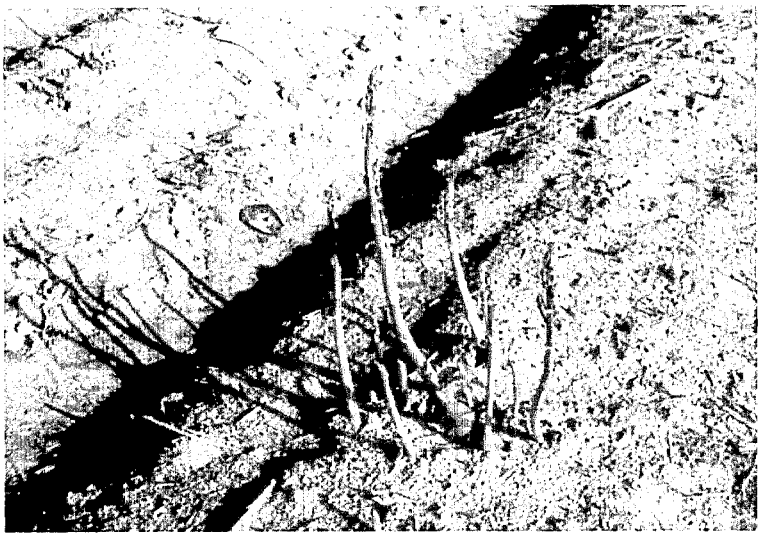
FIG. 3 shows its "earliness" in initiating spears compared to other plants.

The only existing methods of asexual reproduction of asparagus plants for the multiplication of plants of this invention are crown division or tissue culture. The plant of this invention has been asexually reproduced by tissue culture techniques which are more conducive to large scale multiplication of asparagus plants than is crown division.

The color designated hereinafter are approximate and may vary with several factors including soil type, nutrition, climate, and maturity. The colors have been determined by comparison to the colors in "Color Standards and Color Nomenclature" by Robert Ridgway, Washington, D.C., 1912.

PLANT CHARACTERISTICS

Spear: Emerges very early in the spring, fast growing, straight, round, smooth with slow taper. Heads are very tight, taper with the body of the spear, smooth and initiates lateral branches at or above the 16th node when the spears are 12 to 13 inches in height. Bracts are Lumiere Green (Plate XVII) and flush to the spear. Spear color is Biscay Green (Plate XVII).

Foliage: An erect Light Biscay Green (Plate XVII) perennial herb with straight, smooth stems, having many lateral branches. Branches are initiated acropetally as a plant grows in height. A plant three years or older initiates between 25 and 35 stalks that grow to a height between six and seven feet. The average diameter of the stalks at soil level is between three-fourths and one inch. The mature fern is Light Hellebore Green (Plate XVII). The first lateral branch is initiated at or above the 16th node in the spring when the spear is 12 to 13 inches in height. The mature cane is Kildare Green (Plate XXXI) and the cane bract is Light Orchraoeous-Buff (Plate XV).

Inflorescence: One to four, usually two in axils with cladodes. Flowers are Light Greenish Yellow (Plate V) campulate, stamens six, and 0.05 to 0.07 centimeters in length. All flowers are initiated on the older portion of the stem first and mature acropetally.

Fruit: None.

Crown root: Crown a woody rhizome with numerous long fleshy storage roots and fiberous absorptive roots. Fleshy storage roots one-fourth to three-fourths inch in diameter and many feet in length.

We claim:

1. The new and distinct variety of asparagus plant herein described and illustrated and identified by the characteristics enumerated above.

* * * * *